United States Patent

Schreck et al.

[11] Patent Number: 5,864,241
[45] Date of Patent: Jan. 26, 1999

[54] MAGNETIC TRANSDUCER WITH WEAR INDICATOR IN A MAGNETIC DATA STORAGE SYSTEM

[75] Inventors: Erhard Theodor Schreck, San Jose; Clinton David Snyder, Los Gatos; Mike Suk, Milpitas, all of Calif.

[73] Assignee: International Business Machines Corporation, Armonk, N.Y.

[21] Appl. No.: 695,252

[22] Filed: Aug. 8, 1996

[51] Int. Cl.⁶ .............................. G11B 5/48; G01R 27/26
[52] U.S. Cl. .......................... 324/699; 324/210; 360/103
[58] Field of Search .................................. 324/701, 525, 324/555, 660, 661, 699, 210; 340/635, 648; 360/103

[56] References Cited

U.S. PATENT DOCUMENTS

| | | | |
|---|---|---|---|
| 4,024,525 | 5/1977 | Baumgartner | 340/648 |
| 4,316,186 | 2/1982 | Purdy | 340/648 |
| 4,334,188 | 6/1982 | Dudley | 324/133 |
| 4,344,672 | 8/1982 | Harper | 340/648 |
| 4,416,144 | 11/1983 | Chen et al. | 73/12 |
| 4,532,802 | 8/1985 | Yeack-Scranton et al. | 73/432 |
| 4,636,778 | 1/1987 | Corkran et al. | 340/648 |
| 5,038,625 | 8/1991 | Chen | 73/865.9 |
| 5,212,982 | 5/1993 | Macchiarulo | 324/701 |
| 5,410,439 | 4/1995 | Egbert et al. | 360/75 |
| 5,455,730 | 10/1995 | Dovek et al. | 360/113 |
| 5,495,371 | 2/1996 | Munemoto | 360/137 |
| 5,644,450 | 7/1997 | Handa | 360/104 |

FOREIGN PATENT DOCUMENTS

| | | | |
|---|---|---|---|
| 61-85609 | 5/1986 | Japan | G11B 5/187 |
| 1109618 | 9/1984 | U.S.S.R. | 324/701 |

*Primary Examiner*—Maura K. Regan
*Attorney, Agent, or Firm*—Noreen A. Krall

[57] ABSTRACT

A wear indicator is incorporated on the slider of a magnetic transducer in a magnetic storage system for in operation on-the-fly detection of the state of wear of the transducer. The wear indicator involves monitoring a change in an electrical property of an electrical circuit structure as the transducer is worn by abrasion against the magnetic disk medium. In one aspect of the present invention, the resistance (or conductance) of the circuit is monitored during disk drive operations. Part of the resistance (conductance) circuit structure is mounted on the slider and it is physically worn along with the wearing of the transducer. A predetermined change in resistance (or conductance) gives an indication of the predetermined wear limit at which the transducer should be replaced prior to its actual failure. In a specific embodiment, the circuit is configured such that an open circuit (infinite resistance or zero conductance) indicates that the wear limit has been reached. In another aspect of the present invention, the capacitance between a probe mounted on the slider and the magnetic disk is monitored during disk drive operations. The capacitance of the circuit changes as the transducer wears. A predetermined change in the capacitance give an indication of the wear limit at which the transducer should be replaced prior to its complete failure.

21 Claims, 7 Drawing Sheets

MAGNETIC TRANSDUCER WITH WEAR INDICATOR IN A MAGNETIC DATA STORAGE SYSTEM

BACKGROUND OF THE INVENTION

1. Field of the Invention

The present invention relates to a magnetic transducer in a magnetic data storage system, and more particularly to a magnetic transducer having a wear indication feature which improves the reliability, availability and serviceability of the magnetic storage system.

2. Description of the Related Art

Magnetic disk drives are information storage devices which utilize at least one rotatable disk with concentric data tracks containing the information, one or more transducers (or "heads") for reading data from and/or writing data to the various tracks, and a head positioning actuator connected to the transducer for moving it to the desired track and maintaining it over the track centerline during read or write operations. Referring to FIG. 1, which shows a prior art head suspension assembly, the transducer 20 is attached to a slider 26 which is biased against the data surface of the disk 24. In alternative prior art assemblies, the slider may fly slightly above the surface of the disk supported by an air bearing generated by the rotation of the disk. The slider 26 is mounted on a support arm of the positioning actuator (not shown) by way of a suspension 25. The suspension 25 provides dimensional stability between the slider 26 and actuator, and controlled flexibility in slight vertical as well as pitch and roll motions (gimbaled motions) of the slider during its relative motion above the rotating magnetic disk surface.

With a push for higher data densities (the amount of data which can be recorded on a disk), it becomes a challenge to format the disk surface with narrower data tracks and narrower inter-track spacings in order to pack more data tracks on the disk surface. A significant limitation on data density is the spacing between the transducer and the disk surface. Generally, the smaller the spacing between a transducer and a disk, the higher the data density possible, as the magnetic flux in relation to the transducer is more focused at a smaller area on the disk surface so as to improve data resolution. As previously mentioned, one type of transducer in a magnetic disk storage system is designed to be mounted on a slider which rides on a cushion of air or an air bearing generated by the rotating disk in close proximity to the disk surface. For another type of transducer, it is designed to be mounted on a slider with the transducer in contact with the rotating disk surface. The transducer of the latter type is often referred to as contact transducer. With everything else being equal, it is possible to achieve a higher data density using a contact transducer than an air bearing type transducer.

The contact transducer is not without limitation. Referring to FIG. 1, the contact transducer 20 has a tip structure 22 (schematically shown) which is configured to detect a change in magnetic flux when reading data from the magnetic disk 24 and/or cause a change in magnetic flux when writing data onto the magnetic disk 24 as the transducer 20 is moved across the magnetic disk 24. This tip 22 has an operational thickness T in the order of a few microns thick. By nature of a contact transducer, the tip 22 is inevitably subject to wear from abrasion by the magnetic disk 24 once the disk drive has been placed into operation. The slider 26 which is made of a harder material than the tip 22 slows down the wear process to some extent. However, eventually, prolong wear of the transducer tip 22 would lead to inadequate or unreliable transducing functions and ultimate failure of the transducer 20, which would in turn lead to read and/or write failure of the disk drive system thereby putting it out of service. When the transducer fails, data integrity may be affected.

It is therefore desirable for an user of a disk drive system to be able to anticipate the wear induced failure point of the contact transducer 'on-the-fly' during actual operation of the disk drive system, so that data can be safely archived prior to actual transducer failure, and so that the failing transducer or the entire disk drive system may be timely replaced at a convenient time with the least disruption to normal disk drive operations. Further, in accomplishing the foregoing, it is desirable to keep any additional structure to the transducer, slider or the suspension assembly therefor to a minimum. This is to minimize adding weight and inertia to the slider/suspension assembly which would otherwise negatively affect the mechanical performance of the disk drive system and increase complexity of manufacturing.

SUMMARY OF THE INVENTION

The present invention presents a simple wear indicator that is incorporated on the slider for in operation on-the-fly detection of the state of wear of the transducer in a data storage system. The novel feature is relatively easy to be incorporated without adding significant weight to the slider and its suspension and without significantly increasing manufacturing complexity. Feedback from the wear indicator to the storage system's control program allows for greater reliability and availability of the storage system. Conceptually, the novel feature of the present invention involves monitoring a change in one or more electrical properties of an electrical circuit structure as the transducer is subject to wear by abrasion of the magnetic disk medium.

In particular, in accordance with one aspect of the present invention, the resistance (or conductance) of a circuit is monitored during disk drive operations. Part of this circuit structure is mounted on the slider and it is subject to physical wear along with the wearing of the transducer. A predetermined change in resistance (or conductance) gives an indication of the predetermined wear limit at which the transducer should be replaced prior to its actual failure. In a specific embodiment, the circuit is configured such that an open circuit (infinite resistance or zero conductance) indicates that the wear limit has been reached.

In accordance with another embodiment of the present invention, the capacitance between a probe on the slider and the magnetic medium is monitored during disk drive operations. The capacitance changes as the transducer wears. A predetermined change in the capacitance gives an indication of the wear limit at which the transducer should be replaced prior to its complete failure.

DESCRIPTION OF THE ILLUSTRATED EMBODIMENTS

The present description is made for the purpose of illustrating the general principles of the present invention and should not be taken in a limiting sense. The scope of the present invention can best be determined from the appended claims. For example, although the present invention is described in reference to a magnetic disk storage system and in particular one which implements a contact transducer, it will be apparent that the invention may be implemented in other magnetic data storage systems including recording systems such as a magnetic tape drive system or other applications which could take advantage of the wear indicator feature described hereinbelow.

Figure 2:
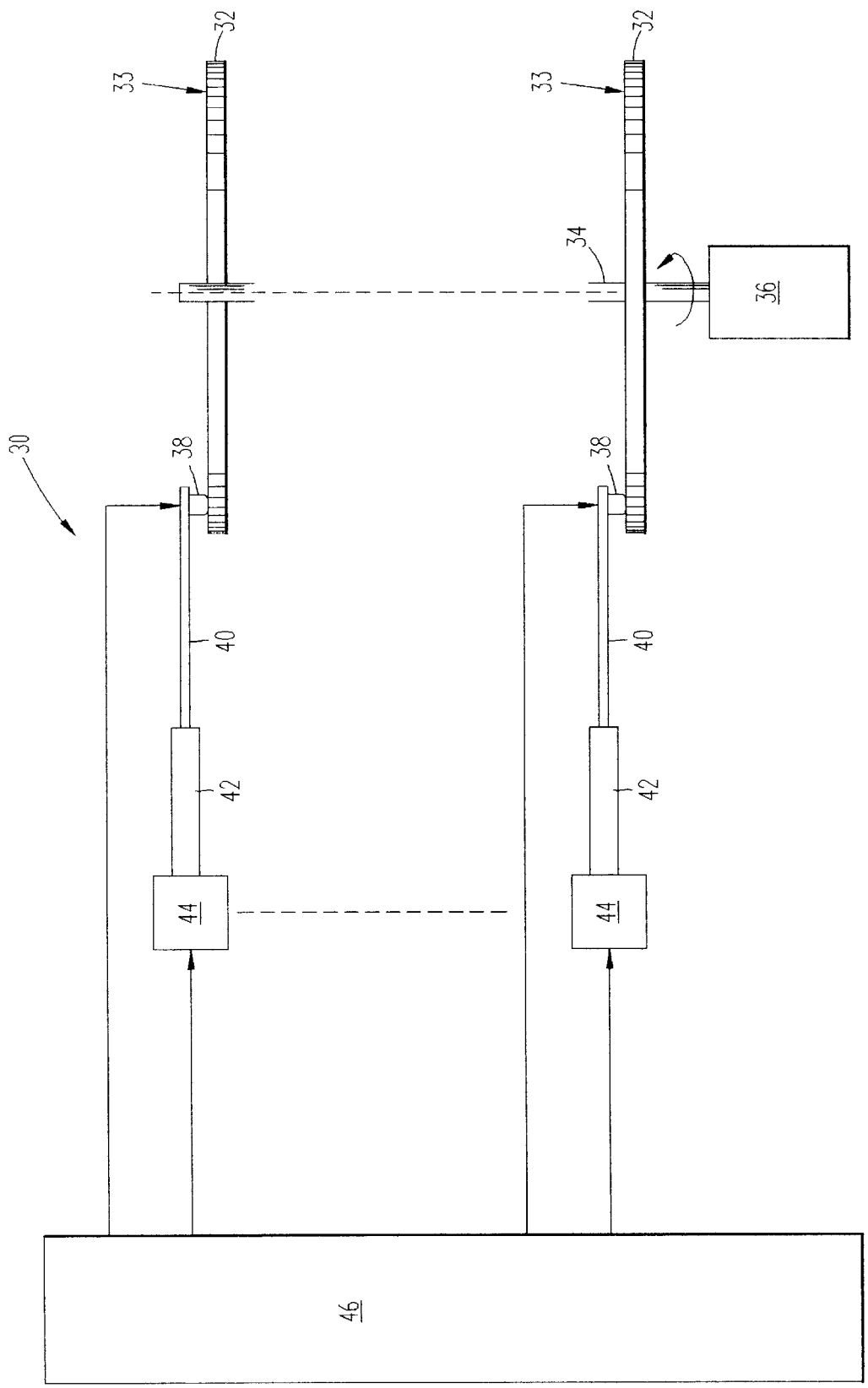
FIG. 2 is a schematic/block diagram of a magnetic disk storage system in which the present invention is implemented.

FIG. 2 illustrates a simplified schematic block diagram of a magnetic disk storage system 30 embodying the present invention for use in an information processing systems such as a computer, for example. The magnetic disk storage system 30 comprises at least one rotatable magnetic disk 32 which is supported on a spindle 34 and rotated by a disk drive motor 36, and at least one slider 38 positioned in close proximity to the magnetic recording medium at the disk surface 33. Data is stored in the magnetic recording medium on each disk 32 in the form of an annular pattern of concentric data tracks (not shown). Each slider 38 is an assembly containing one or more magnetic read and write transducers (not shown). The slider 38 is mounted to a suspension 40 which is connected to an actuator means 44 by way of an actuator arm 42. As the disk 32 rotates, the slider 38 is controlled to move across the disk surface 33 by the actuator means 44 so that the slider 38 may access different portions of the disk surface 33 where desired data is recorded or read. The suspension 40 provides a slight spring force which biases the slider 38 against the disk surface 33 and controls flexibility in slight vertical as well as roll and pitch movements of the slider 38 relative to the rotating disk surface 33. The actuator means as shown in FIG. 2 may be a voice coil motor (VCM), for example. The reading/writing of data and the operations of the various components (e.g. actuator means 44 and drive motor 36) of the magnetic disk storage system 30 are controlled by a control unit 46. In addition, the control unit 46 also includes a detection device for the wear limit indicator as will be explained below.

Figure 1:
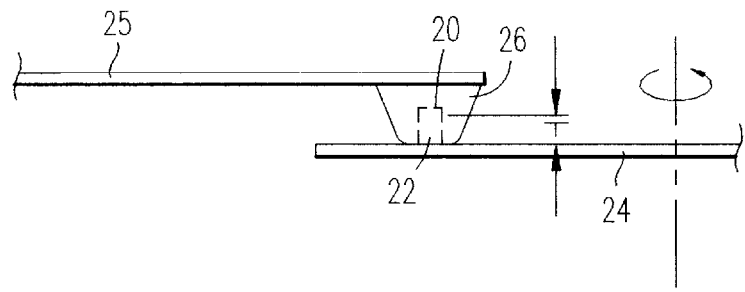
FIG. 1 is a schematic side view of a prior art slider/suspension assembly.
Figure 3:
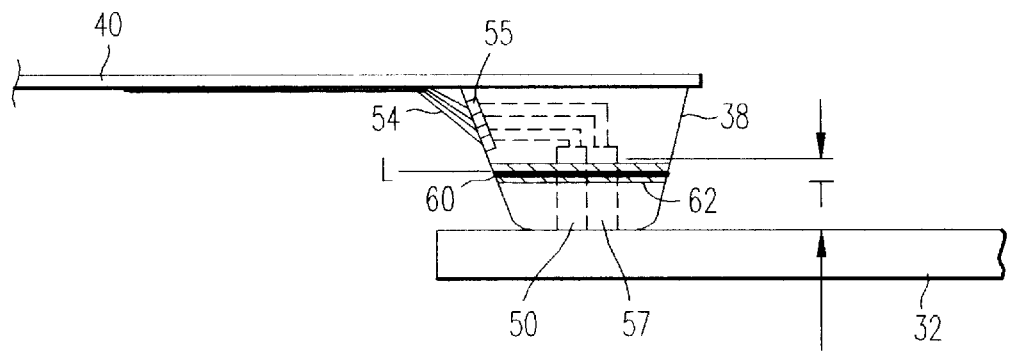
FIG. 3 is a schematic side view of a slider/suspension assembly having a wear limit indicator based on resistance measurement in accordance with one embodiment of the present invention.

FIGS. 3 schematically illustrates more closely the slider region. In this particular embodiment shown, there are a read transducer 50 and a separate write transducer 52. (The read and write transducers 52, 54 are schematically shown in the figures for simplicity of illustration. Their actual sizes and locations may be different, but they do not affect the understanding of the concept of the present invention.) The read transducer 50 may be of the magneto-resistive type (the resistance of a magneto-resistive read transducer changes in the presence of magnetic flux changes) and the write transducer 52 may be of the inductive type (the magnetic flux changes with a change in current through the inductive transducer). Alternative, a single inductive transducer may be used which performs both read and write functions (see discussion in connection with FIG. 7 below). The read and write transducers 52, 54 and slider 38 may be formed using processes (including, for example, photo lithographic, deposition and subtractive etching processes) known in the art which taken alone do not form a part of the present invention. Electrical leads 54 are connected to transducer contact pads 55 on the slider 38; one pair of the leads being in electrical connection with the read transducer, and the other pair of the leads being in electrical connection with the write transducer.

The transducers 50, 52 have tips of a certain useful thickness (in the order of several microns; e.g., less than 5 microns). Should the tips wear through their useful thickness as a result of abrasion from the magnetic disk 32, the transducers 50, 52 will fail. For reasons earlier mentioned, it is desirable to set a wear limit L for the transducers 50, 52 (within their useful thickness T) prior to their complete failure and provide a means of indicating that this wear limit has been reached during operation of the disk drive system.

In accordance with a first embodiment of the present invention illustrated in FIG. 3, a wear limit indicator 50 in the form of a strip of electrically conductive material is formed around the sides of the slider 38 as shown. This strip 60 is connected to an electrical circuit which allows the detection of resistance or conductance changes in the strip. As the slider 38 and the transducers 50, 52 are worn by abrasive contact with the magnetic disk medium, the strip of material will wear and will eventually be physically broken at some point (i.e., open circuit). As such, the strip 60 should be positioned on the slider 38 such that its breaking point corresponds to the wear limit L of the transducers 50, 52. The resistance or conductance of the open circuit in the strip 60 would indicate that this wear limit has been reached. FIG. 3 illustrates by way of example the situation where the read and write transducers have the same wear limit L. If one of the transducers has a smaller wear limit, the strip 60 should be positioned to correspond to the wear limit of the transducer with the smaller wear limit.

The material of the wear limit indicator strip 60 may be a conductive metal, but preferably a fairly resistive material (e.g., Nichrome) such that the resistance of the entire strip 60 would be ten to several thousand ohms. In the example shown, the total length of the strip 60 is in the order of 200 microns, of which approximately 100 microns is within the pad, and its width is in the order of 8–12 microns. The total thickness of the strip is in range of 80–120 angstroms, and preferably about 100 angstroms. The total resistance of the circuit in this example using this material and these dimensions is 2 Kohms. The purpose for using a resistive material would become apparent from the discussion below in connection with FIG. 6. A layer of insulative material 62 (e.g., photo resist or alumina) separates the strip 60 from the slider 38.

The leads 64 to the wear indicator strip are electrically connected to a resistance or conductance measuring device in the control unit 46 of the disk drive system 30, depending on whether resistance or conductance is relied upon as an indication of the change in electrical properties of the wear limit indicator. The specific electrical circuit for the wear limit indicator depends on the type of transducers mounted on the slider 38 and the scheme of wear limit detection relied upon (resistance or conductance).

Figure 6:
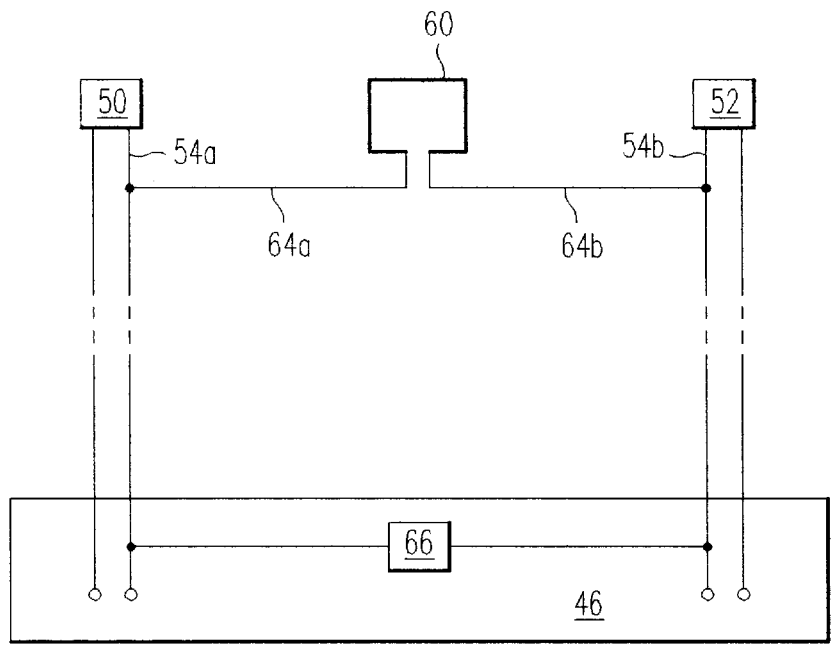
FIG. 6 is a circuit diagram of the wear limit indicator implementation for the embodiment of FIG. 3.
Figure 7:
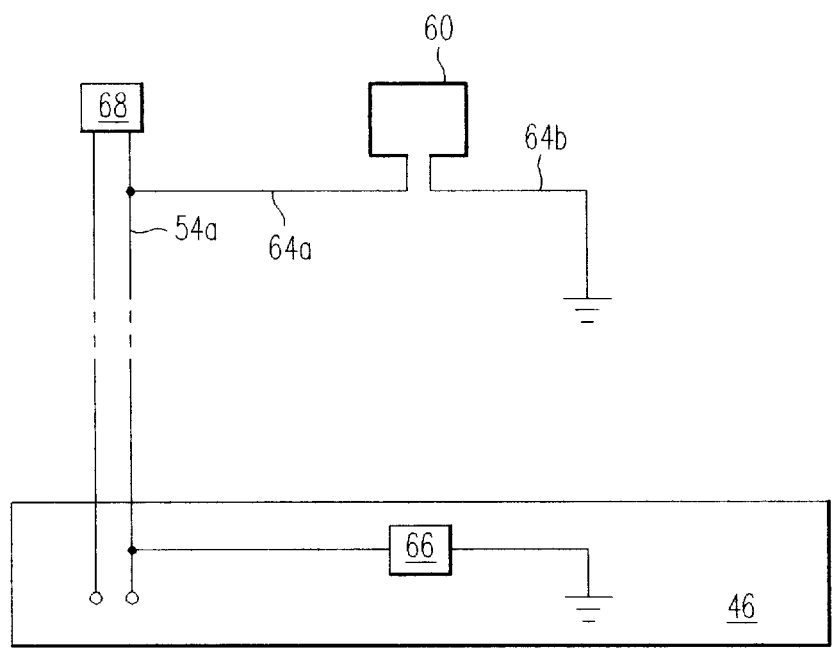
FIG. 7 is a circuit diagram of the wear limit indicator implementation for a single inductive transducer.
Figure 8:
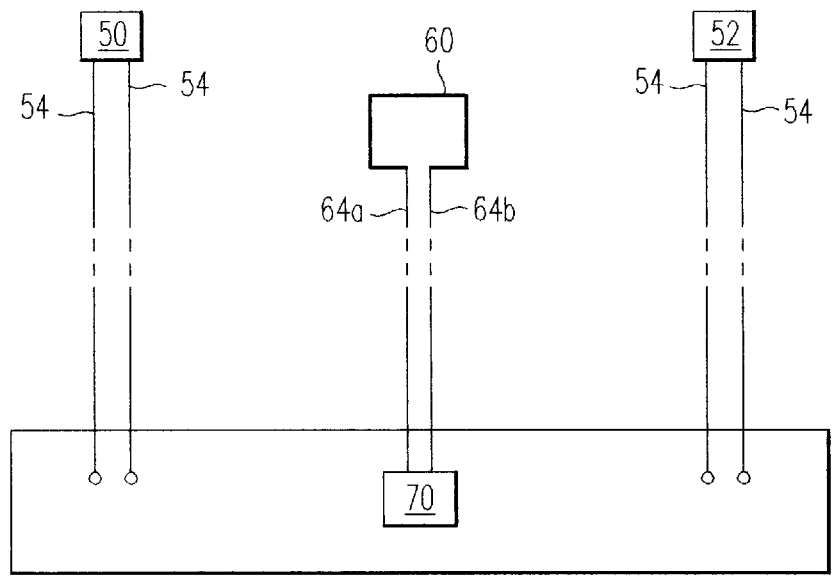
FIG. 8 is a circuit diagram of the wear limit indicator implementation which is based on conductance measurement.
Figure 11:
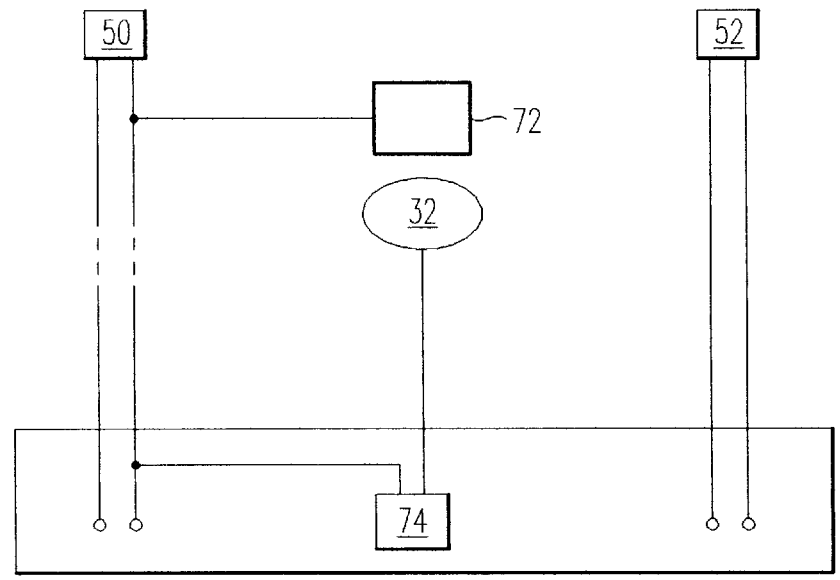
FIG. 11 is a circuit diagram of the wear limit indicator implementation for the embodiment of FIG. 9.

The different electrical circuits for the wear limit indicator is now explained in reference to FIGS. 6–8. FIG. 6 shows the configuration in which resistance of the strip 60 is measured for wear limit detection and the read transducer 50 is of the magneto-resistive type and the write transducer 52 is of the inductive type. In this configuration, one lead 64a to the wear limit indicator strip 60 is connected to a read transducer lead 54a and the other lead 64b to the strip 60 is connected to a write transducer lead 54b. The interconnection of the leads 54a and 54b by the strip 60 does not affect the read and write functions of the read and write transducers 50, 52, owing to the relative high resistance of the strip 60 compared to the low resistance of the transducers which is in the order of several ohms. The transducer leads 54a and 54b are connected to a resistance measuring device 66 in the control unit 46.

In the case in which resistance of the strip 60 is measured for wear limit detection and a single inductive transducer 68 is used for both read and write functions, the circuit shown in FIG. 7 would be appropriate. In this configuration, one lead 64a of the wear limit indicator strip 60 is connected to a transducer lead 54a and the other lead 64b of the strip is connected to ground. The resistance measuring device 66 in the control unit 46 is connected to the lead 54a and ground.

Figure 4:
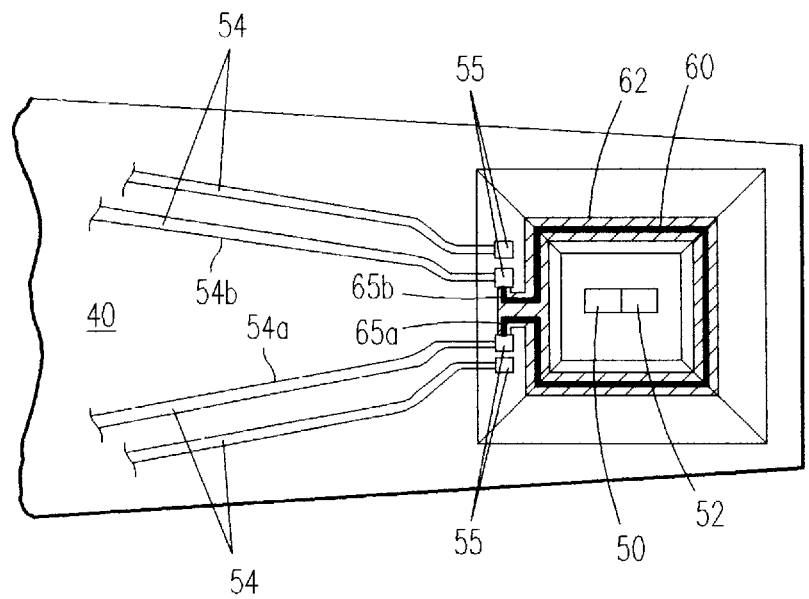
FIG. 4 is a schematic bottom view of the slider/suspension assembly of FIG. 3.

For both the above two configurations, the leads of the transducers can be conveniently made use of by the wear limit indicator strip 60 to make connection to the resistance measuring device 66 in the control unit 46. This is desirable as it eliminates the need to use full lengths of separate leads to connect the strip 60 on the slider 38 directly to the control unit 46, thereby simplifying the manufacturing process and keeping to a minimum the added weight to the slider/suspension assembly as a result of addition of the wear limit indicator feature. It is noted that the short connections from the strip 60 to the transducer leads 54 may be in the form of metal traces formed on the slider 38 and/or suspension 40 using any known processes involving, for example, photolithography, deposition, and/or etching steps. For example in FIG. 4, the leads 64a and 64b may be in the form of short surface traces 65a and 65b formed on the slider to connect the leads 64 of the strip 60 to the appropriate contact pads 55.

In the case of detection of the wear limit based on measurement of the conductance of the wear limit indicator strip, separate leads for the wear limit indicator strip would be required, regardless of the type of transducers used. Referring to FIG. 8, two separate leads 64a and 64b from the strip 60 are connected directly to a conductance measuring device 70 in the control unit 46.

Figure 5:
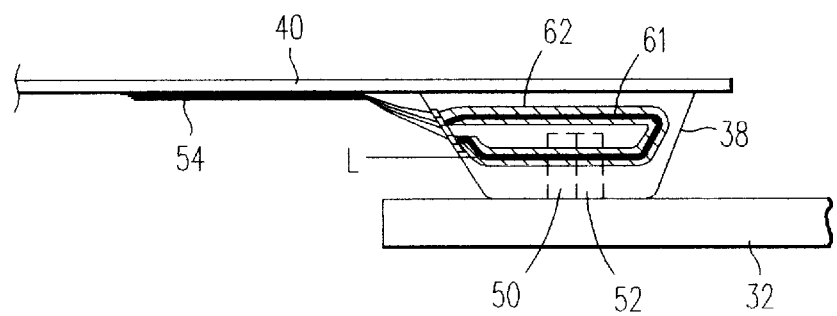
FIG. 5 is a schematic side view of a slider/suspension assembly having a wear limit indicator based on resistance measurement in accordance with another embodiment of the present invention.

Referring back to FIG. 4, the strip 60 is positioned around the periphery of the slider 38 so that any uneven wear occurring more at any corner or side of the slider 38 may be detected. Alternatively, it may be configured as a strip 61 on only one side of the slider 38 as shown in FIG. 5. This configuration, however, might not provide an accurate indication of the wear limit of the transducers 50, 52 should uneven wear occurs.

In alternative embodiments, the strip 60 may be disposed about the edge of the slider 38 or a few microns in from the edge of the slider. The strip could be placed in various locations about the slider, so long as the strip 60 either encloses or substantially encloses the read/write elements. If the strip 60 does not completely enclose the read/write elements, it should enclose three sides of the read/write elements.

It is noted that the aforedescribed embodiments are examples illustrating the general principles of the present invention. While the wear limit is indicated by an open circuit in the wear limit indicator strip, it is contemplated that the present invention is equally applicable to a detection of the wear limit by monitoring a gradual change in the resistance or conductance in the strip (from a reference resistance or conductance at the time the transducer is placed into service) as it is being worn by abrasion by the magnetic disk. The wear limit may be set at a point prior to an open circuit involving the wear limit indicator strip.

Figure 9:
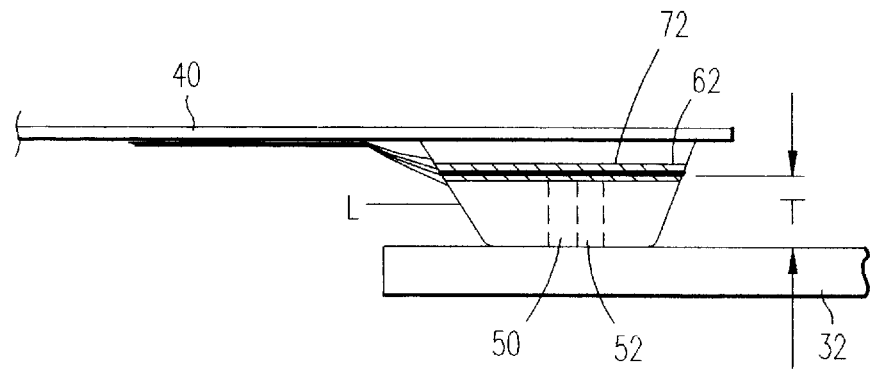
FIG. 9 is a schematic side view of a slider/suspension assembly having a wear limit indicator which is based on capacitance measurement.
Figure 10:
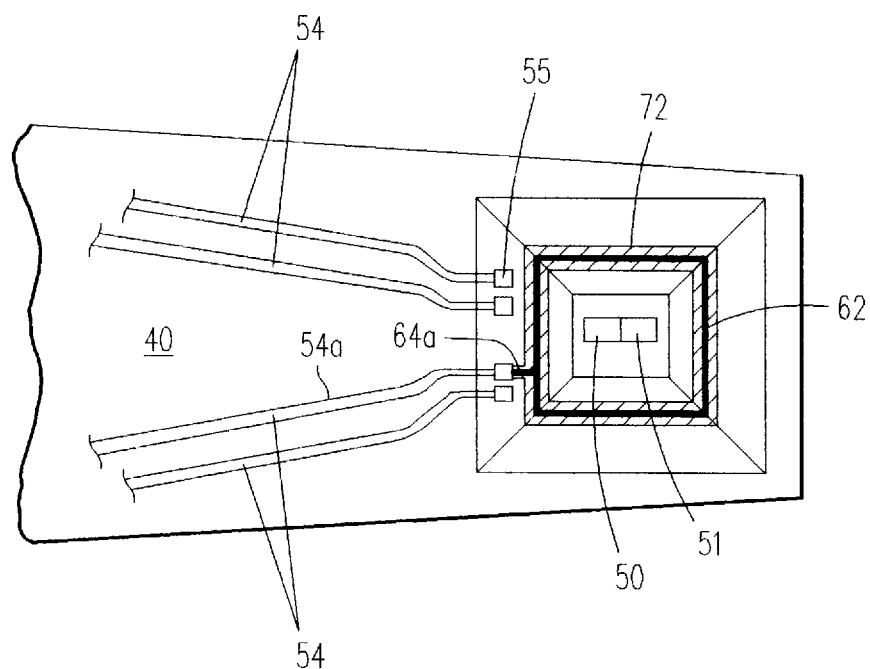
FIG. 10 is a schematic bottom view of the slider/suspension assembly of FIG. 9.

In another embodiment of the present invention shown in FIGS. 9 and 10, the change in capacitance between a conductive surface and a probe on the slider 38 is relied upon to give an indication of the status of wear of the transducers 50, 52. The conductive surface may be the magnetic media, a conductive overcoat, and/or a conductive substrate on the slider. The probe may be in the form of a closed loop 72 of metal (having a width in the order of 10 microns) around the sides of the slider 38 formed in a manner similar to the wear limit indicator strip 60 in the earlier embodiment. As the slider 38 and transducers 50, 52 wear from abrasion by the magnetic disk 32, the spacing between the loop 72 and magnetic disk 32 changes, thereby changing the capacitance at the spacing. Referring also to FIG. 10, the capacitance between this loop 72 and the magnetic disk 32 is monitored by a conductance measuring device 74 in the control unit 46. As in the earlier embodiments, one lead 54a of the transducer 50 may be made use of to make the electrical connection between the loop 72 and the control unit 46.

It can be appreciated that the loop 72 should be positioned on the slider at a point beyond the wear limit L as abrasion of the loop is not contemplated. The wear limit of the transducer is detected to have been reached at a predetermined capacitance measured.

Figure 12:
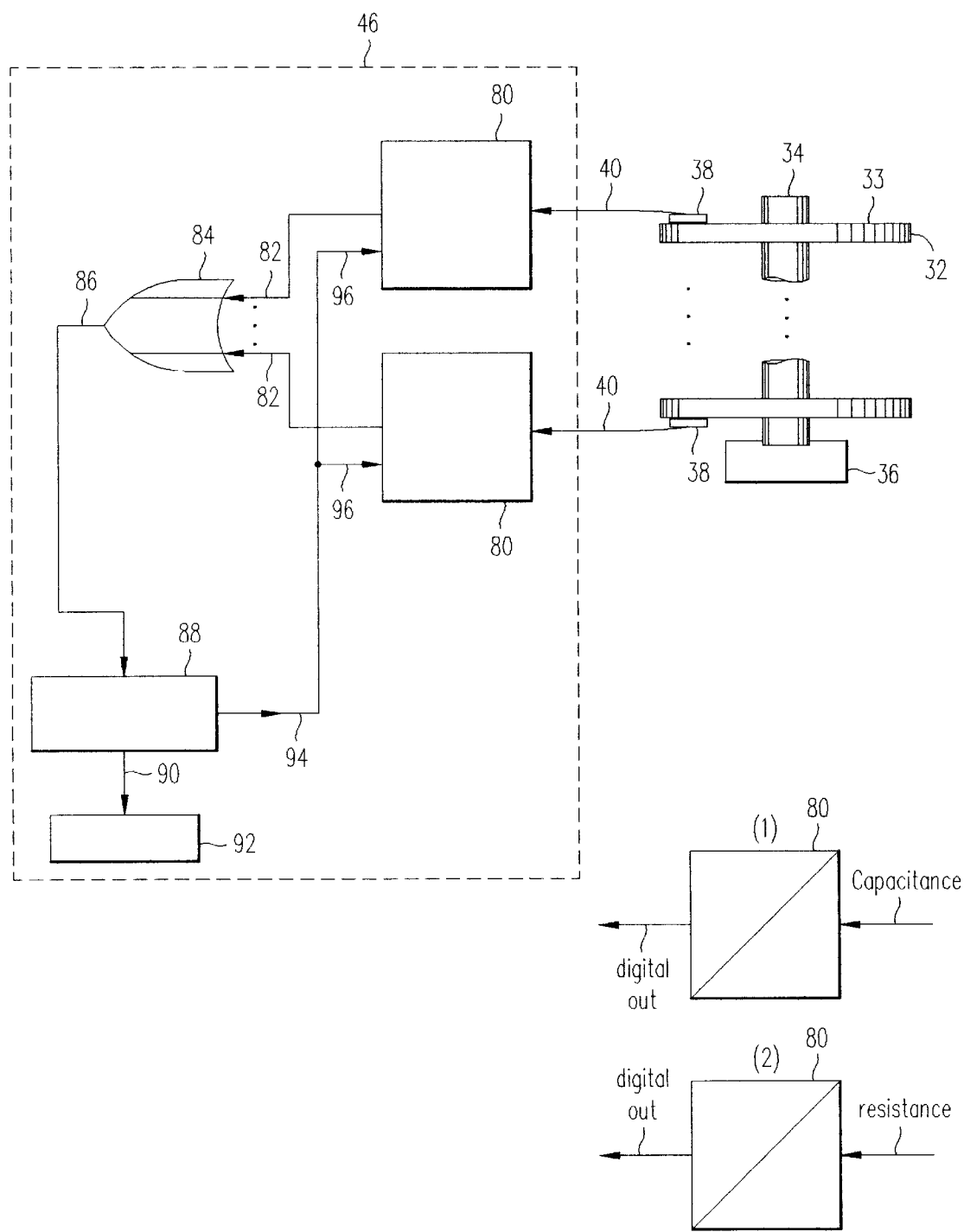
FIG. 12 is a flow diagram of a storage system having a wear indicator for on-the-fly detection of wear of the transducer in the storage system.

With reference now to FIG. 12, a flow diagram of a disk drive system including the wear indicator is shown. At least one rotatable magnetic disk 32 is supported by spindle 34 and rotated by disk drive motor 36. At least one slider 38 is positioned in close proximity to the magnetic recording medium at the disk surface. As the disk rotates, the wear limit indicator 50 (as shown previously in FIG. 3) sends a signal along the sensor leads over suspension 40 to control unit 46. Control unit 46 comprises at least one sensor signal processor 80, which receives the signal from the wear limit indicator. The sensor signal processor 80 sends the boolean representation of the signal into OR gate 84, where the signal is OR'd with the signals from other suspension assemblies (if any). The signal is then transmitted over line 86 into file processor 88. The file processor 88 determines from the signal whether or not the wear limit indicator has reached its threshold value. If the file processor 88 determines that the wear limit has been reached, then the file processor 88 sets the status flag at 92. If the wear limit has not yet been reached, then along path 94, the file processor 88 continues to enable the wear sensors. It is noted that the sensor signal processing units 80 are adapted to receive a signal based on the capacitance between a probe on the slider and the magnetic medium and convert it into a digital signal, or to receive a signal based on the resistance of the circuit and convert it to a digital signal.

The wear limit indicator of the present invention has been described in reference to contact type transducers which are in constant contact with the magnetic disk during data reading and writing operations. It is understood that the present invention may be implemented for a 'flying' transducer of the type which rides on an air bearing against the magnetic disk. Such flying type transducer is also subject to wear of the magnetic disk at least during initial acceleration and final deceleration of the disk when the disk drive system is turned on and off.

While the present invention has been particularly shown and described with reference to the illustrated embodiments thereof, it will be understood by those skilled in the art that various changes in form and detail may be made therein without departing from the spirit, scope and teaching of the invention. Accordingly, the invention herein disclosed is to be considered merely as illustrative and limited in scope only as specified in the appended claims.

We claim:

1. A magnetic transducing assembly for transducing a magnetic medium in a magnetic disk storage system, comprising:

at least one slider comprising a transducer which includes a read transducer, a read transducer lead in electrical connection with the read transducer, a write transducer and a write transducer lead in electrical connection with the write transducer, said transducer having a useful thickness which defines a useful life of the transducer, wherein the transducer is subject to wear by the magnetic medium during relative motions of the slider and the magnetic medium and wherein the useful life of the transducer is spent when its useful thickness has been worn through; and a wear sensor comprising a strip of electrically conductive material formed on the slider at a location defining the wear limit of the transducer, wherein one end of the wear sensor is connected to the read transducer lead and a second end of the wear sensor is connected to the write transducer lead, such that when the useful thickness is worn the changing electrical properties of the strip are detectible by a detection circuit comprised of said electrical leads.

2. A magnetic transducing assembly as in claim 1, wherein the detection circuit monitors a change in electrical resistance or conductance of the sensor.

3. A magnetic transducing assembly as in claim 2, wherein the detection circuit monitors a change from close to open circuit in the sensor which corresponds to a wear limit of the transducer within its useful thickness.

4. A magnetic transducing assembly as in claim 3, wherein said slider has a bottom surface and sides, the slider supporting the useful thickness of the transducer at its bottom surface, and wherein the sensor is attached near the edge of at least one side of the slider.

5. A magnetic transducing assembly as in claim 4, wherein the strip of material is positioned about the periphery of the transducers, such that the strip has a similar wear rate as the transducers.

6. A magnetic transducing assembly as in claim 1, wherein the detection circuit includes capacitance means for defining an electrical capacitance which changes with wear of the transducer, and wherein the detection circuit monitors a change in capacitance as a result of such wear, thereby giving an indication of the wear status of the transducer.

7. A magnetic transducing assembly as in claim 6, wherein the capacitance means includes a probe positioned in a fixed relation to the transducer.

8. A suspension assembly for supporting a slider for transducing a magnetic medium in a magnetic storage system, comprising:

a suspension member;

a slider supported by the suspension member;

a transducer supported on the slider for transducing the magnetic medium, the transducer comprising a read transducer, a read transducer lead in electrical connection with the read transducer, a write transducer and a write transducer lead in electrical connection to the write transducer, said transducer having a useful thickness which defines a useful life of the transducer, wherein the transducer is subject to wear by the magnetic medium during relative motions of the slider and the magnetic medium and wherein the useful life of the transducer is spent when its useful thickness has been worn through; and a wear sensor comprising a strip of electrically conductive material formed on the slider at a location defining the wear limit of the transducer, wherein one end of the wear sensor is connected to the read transducer lead and a second end of the wear sensor is connected to the write transducer lead, such that when the useful thickness is worn the changing electrical properties of the strip are detectible by a detection circuit comprised of said electrical leads.

9. A suspension assembly as in claim 8, wherein the detection circuit monitors a change in electrical resistance or conductance of the sensor.

10. A suspension assembly as in claim 9, wherein the detection circuit monitors a change from close to open circuit in the sensor which corresponds to a wear limit of the transducer within its useful thickness.

11. A suspension assembly as in claim 10, wherein said slider has a bottom surface and sides, the slider supporting the useful thickness of the transducer at its bottom surface, and wherein the sensor is attached near the edge of at least one side of the slider.

12. A suspension assembly as in claim 11, wherein the strip of material is positioned about the periphery of the transducers, such that the strip has a similar wear rate as the transducers.

13. A suspension assembly as in claim 8, wherein the detection circuit includes capacitance means for defining an electrical capacitance which changes with wear of the transducer, and wherein the detection circuit monitors a change in capacitance as a result of such wear, thereby giving an indication of the wear status of the transducer.

14. A suspension assembly as in claim 13, wherein the capacitance means includes a probe positioned in a fixed relation to the transducer.

15. A magnetic storage system comprising:

a magnetic storage medium having a plurality of tracks for receiving data;

drive means for moving the magnetic storage medium;

a slider including at least one transducer maintained in a transducing position relative to said magnetic storage medium during relative motions between said slider and said magnetic storage medium, said transducer comprising a read transducer, a read transducer lead in electrical connection with the read transducer, a write transducer and a write transducer lead in electrical connection with the write transducer, said transducer having a useful thickness which defines a useful life of the transducer, wherein the transducer is subject to wear by the magnetic medium during relative motions of the slider and the magnetic medium and wherein the useful life of the transducer is spent when its useful thickness has been worn through;

a wear sensor comprising a strip of electrically conductive material formed on the slider at a location defining the wear limit of the transducer, wherein one end of the wear sensor is connected to the read transducer lead and a second end of the wear sensor is connected to the write transducer lead, such that when the useful thickness is worn the changing electrical properties of the strip are detectible by a detection circuit comprised of said electrical leads;

actuator means coupled to said slider for moving said slider relative to the magnetic storage medium to selected tracks on said magnetic storage medium, said actuator means including a suspension assembly which supports the slider at one end thereof; and control means for controlling the operation of the drive means, wear sensor, actuator means and transducing of data with respect to the magnetic storage medium.

16. A magnetic storage system as in claim 15, wherein the detection circuit monitors a change in electrical resistance or conductance of the sensor.

17. A magnetic storage system as in claim 16, wherein the detection circuit monitors a change from close to open circuit in the sensor which corresponds to a wear limit of the transducer within its useful thickness.

18. A magnetic storage system as in claim 17, wherein said slider has a bottom surface and sides, the slider supporting the useful thickness of the transducer at its bottom surface, and wherein the sensor is attached near the edge of at least one side of the slider.

19. A magnetic storage system as in claim 18, wherein the strip of material is positioned about the periphery of the transducers, such that the strip has a similar wear rate as the transducers.

20. A magnetic storage system as in claim 15, wherein the detection circuit includes capacitance means for defining an electrical capacitance which changes with wear of the transducer, and wherein the detection circuit monitors a change in capacitance as a result of such wear, thereby giving an indication of the wear status of the transducer.

21. A magnetic storage system as in claim 20, wherein the capacitance means includes a probe positioned in a fixed relation to the transducer.

* * * * *